(12) United States Patent
Polack et al.

(10) Patent No.: US 7,939,319 B2
(45) Date of Patent: May 10, 2011

(54) TOOL FOR THE TRANSFER AND PRODUCTION OF PROTEINS USING THE PSEUDOMONAS TYPE III SECRETION SYSTEM

(75) Inventors: Benoit Polack, Saint Martin le Vinoux (FR); Bertrand Toussaint, Saint Egreve (FR); Lauriane Quenee, La Tronche (FR)

(73) Assignee: Universite Joseph Fourier, Grenoble (FR)

( * ) Notice: Subject to any disclaimer, the term of this patent is extended or adjusted under 35 U.S.C. 154(b) by 967 days.

(21) Appl. No.: 11/433,391

(22) Filed: May 12, 2006

(65) Prior Publication Data
US 2008/0187520 A1    Aug. 7, 2008

Related U.S. Application Data

(63) Continuation-in-part of application No. PCT/FR2004/050564, filed on Nov. 4, 2004.

(30) Foreign Application Priority Data

Nov. 13, 2003 (FR) ..................... 03 13286

(51) Int. Cl.
C12N 15/00 (2006.01)
C12N 15/03 (2006.01)
C12N 15/11 (2006.01)
C12N 15/63 (2006.01)
C12N 15/78 (2006.01)

(52) U.S. Cl. .............. 435/320.1; 435/69.1; 435/252.34; 435/471; 536/23.1; 536/23.4; 536/24.1

(58) Field of Classification Search .................. None
See application file for complete search history.

(56) References Cited

U.S. PATENT DOCUMENTS 5,965,381 A   10/1999   van der Bruggen et al. ..... 435/29
6,306,387 B1  10/2001   Galan ......................... 424/93.2

OTHER PUBLICATIONS

Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Zhang et al, A Leucine-Rich Motif Targets *Pseudomonas aeruginosa* ExoS within Mammalian Cells, Infection and Immunity, Dec. 2005, p. 7938-7945.*
Pederson et al, Intracellular localization modulates targeting of ExoS, a type III cytotoxin, to eukaryotic signalling proteins, Molecular Microbiology (2002) 46 (5), 1381-1390.*
Polack et al., "Protein Delivery by *Pseudomonas* Type III Secretion System: Ex Vivo Complementation of $p67^{phox}$-Deficient Chronic Granulomatous Disease," Biochemical and Biophysical Research Communications 275, pp. 854-858 (2000).
Pederson et al., "Intracellular localization and processing of *Pseudomonas aeruginos* ExoS in eukaryotic cells," Molecular Microbiology 37(2), pp. 287-299 (2000).
Pederson et al., "Intracellular localization modulates targeting of ExoS, a type III cytotoxin, to eukaryotic signaling proteins," Molecular Microbiology 46(5), pp. 1381-1390 (2002).
Krall et al., "Intracellular targeting of two type III secreted cytokines," Abstracts of the General Meeting of the American Society for Microbiology, 103, pp. 42-43 (2003).
Cornelis et al., "The Yersinia Yop virulon: A bacterial system for subverting eukaryotic cells," Molecular Microbiology 23(5), pp. 861-867 (1997).
Sory et al., "Identification of the YopE and YopH domains required for secretion and internalization into the cytosol of macrophages, using the *cyaA* gene fusion approach," Proc. Natl. Acad. Sci, USA 92, pp. 11998-12002 (1995).
Yahr et al., "Identification of Type III Secreted Products of the *Pseudomonas aeruginosa* Exoenzyme S Regulon," Journal of Bacteriology 179(22), pp. 7165-7168 (1997).

* cited by examiner

Primary Examiner — Maria Marvich
(74) Attorney, Agent, or Firm — Heslin Rothenberg Farley & Mesiti, P.C.

(57) ABSTRACT

The present invention provides a vector for expression of a chimeric protein which is the result of the fusion between the N-terminal end of ExoS of *Pseudomonas aeruginosa* and an amino acid sequence of interest, the N-terminal end of ExoS corresponding to the N-terminal end of the chimeric protein. The vector contains the following from 5' to 3':
  a promoter,
  a nucleic acid comprising a nucleotide sequence encoding at least the 48 (SEQ ID 4) and at the most the 96 (SEQ ID 6) amino acids of the N-terminal end of ExoS; or any sequence of the same size that is at least 70% identical thereto and that has a secretion activity at the same level as that of ExoS,
  a nucleic acid comprising a nucleotide sequence encoding the amino acid sequence of interest.

9 Claims, 7 Drawing Sheets

SEQUENCE LISTING

```
<160> NUMBER OF SEQ ID NOS: 8

<210> SEQ ID NO 1
<211> LENGTH: 17
<212> TYPE: PRT
<213> ORGANISM: Pseudomonas aeruginosa
<220> FEATURE:
<221> NAME/KEY: misc_feature
<222> LOCATION: 1..17
<223> OTHER INFORMATION: corresponds to the first 17 aa of ExoS

<400> SEQUENCE: 1

Met His Ile Gln Ser Leu Gln Gln Ser Pro Ser Phe Ala Val Glu Leu
1               5                   10                  15

His

<210> SEQ ID NO 2
<211> LENGTH: 30
<212> TYPE: PRT
<213> ORGANISM: Pseudomonas aeruginosa
<220> FEATURE:
<221> NAME/KEY: misc_feature
<222> LOCATION: 1..30
<223> OTHER INFORMATION: corresponds to the first 30 aa of ExoS
```

-continued

<400> SEQUENCE: 2

Met His Ile Gln Ser Leu Gln Gln Ser Pro Ser Phe Ala Val Glu Leu
1               5                   10                  15

His Gln Ala Ala Ser Gly Arg Leu Gly Gln Ile Glu Ala Arg
            20                  25                  30

<210> SEQ ID NO 3
<211> LENGTH: 42
<212> TYPE: PRT
<213> ORGANISM: Pseudomonas aeruginosa
<220> FEATURE:
<221> NAME/KEY: misc_feature
<222> LOCATION: 1..42
<223> OTHER INFORMATION: corresponds to the first 42 aa of ExoS

<400> SEQUENCE: 3

Met His Ile Gln Ser Leu Gln Gln Ser Pro Ser Phe Ala Val Glu Leu
1               5                   10                  15

His Gln Ala Ala Ser Gly Arg Leu Gly Gln Ile Glu Ala Arg Gln Val
            20                  25                  30

Ala Thr Pro Ser Glu Ala Gln Gln Leu Ala
        35                  40

<210> SEQ ID NO 4
<211> LENGTH: 48
<212> TYPE: PRT
<213> ORGANISM: Pseudomonas aeruginosa
<220> FEATURE:
<221> NAME/KEY: misc_feature
<222> LOCATION: 1..48
<223> OTHER INFORMATION: corresponds to the first 48 aa of ExoS

<400> SEQUENCE: 4

Met His Ile Gln Ser Leu Gln Gln Ser Pro Ser Phe Ala Val Glu Leu
1               5                   10                  15

His Gln Ala Ala Ser Gly Arg Leu Gly Gln Ile Glu Ala Arg Gln Val
            20                  25                  30

Ala Thr Pro Ser Glu Ala Gln Gln Leu Ala Gln Arg Gln Asp Ala Pro
        35                  40                  45

<210> SEQ ID NO 5
<211> LENGTH: 54
<212> TYPE: PRT
<213> ORGANISM: Pseudomonas aeruginosa
<220> FEATURE:
<221> NAME/KEY: misc_feature
<222> LOCATION: 1..54
<223> OTHER INFORMATION: corresponds to the first 54 aa of ExoS

<400> SEQUENCE: 5

Met His Ile Gln Ser Leu Gln Gln Ser Pro Ser Phe Ala Val Glu Leu
1               5                   10                  15

His Gln Ala Ala Ser Gly Arg Leu Gly Gln Ile Glu Ala Arg Gln Val
            20                  25                  30

Ala Thr Pro Ser Glu Ala Gln Gln Leu Ala Gln Arg Gln Asp Ala Pro
        35                  40                  45

Lys Gly Glu Gly Leu Leu
    50

<210> SEQ ID NO 6
<211> LENGTH: 96
<212> TYPE: PRT
<213> ORGANISM: Pseudomonas aeruginosa

```
<220> FEATURE:
<221> NAME/KEY: misc_feature
<222> LOCATION: 1..96
<223> OTHER INFORMATION: corresponds to the first 96 aa of ExoS

<400> SEQUENCE: 6

Met His Ile Gln Ser Leu Gln Gln Ser Pro Ser Phe Ala Val Glu Leu
1               5                   10                  15

His Gln Ala Ala Ser Gly Arg Leu Gly Gln Ile Glu Ala Arg Gln Val
            20                  25                  30

Ala Thr Pro Ser Glu Ala Gln Gln Leu Ala Gln Arg Gln Asp Ala Pro
        35                  40                  45

Lys Gly Glu Gly Leu Leu Ala Arg Leu Gly Ala Ala Leu Val Arg Pro
    50                  55                  60

Phe Val Ala Ile Met Asp Trp Leu Gly Lys Leu Leu Gly Ser His Ala
65                  70                  75                  80

Arg Thr Gly Pro Gln Pro Ser Gln Asp Ala Gln Pro Ala Val Met Ser
                85                  90                  95

<210> SEQ ID NO 7
<211> LENGTH: 129
<212> TYPE: PRT
<213> ORGANISM: Pseudomonas aeruginosa
<220> FEATURE:
<221> NAME/KEY: misc_feature
<222> LOCATION: 1..129
<223> OTHER INFORMATION: corresponds to the first 129 aa of ExoS

<400> SEQUENCE: 7

Met His Ile Gln Ser Leu Gln Gln Ser Pro Ser Phe Ala Val Glu Leu
1               5                   10                  15

His Gln Ala Ala Ser Gly Arg Leu Gly Gln Ile Glu Ala Arg Gln Val
            20                  25                  30

Ala Thr Pro Ser Glu Ala Gln Gln Leu Ala Gln Arg Gln Asp Ala Pro
        35                  40                  45

Lys Gly Glu Gly Leu Leu Ala Arg Leu Gly Ala Ala Leu Val Arg Pro
    50                  55                  60

Phe Val Ala Ile Met Asp Trp Leu Gly Lys Leu Leu Gly Ser His Ala
65                  70                  75                  80

Arg Thr Gly Pro Gln Pro Ser Gln Asp Ala Gln Pro Ala Val Met Ser
                85                  90                  95

Ser Ala Val Val Phe Lys Gln Met Val Leu Gln Gln Ala Leu Pro Met
                100                 105                 110

Thr Leu Lys Gly Leu Asp Lys Ala Ser Glu Leu Ala Thr Leu Thr Pro
            115                 120                 125

Glu

<210> SEQ ID NO 8
<211> LENGTH: 8
<212> TYPE: PRT
<213> ORGANISM: Artificial
<220> FEATURE:
<221> NAME/KEY: misc_feature
<222> LOCATION: 1..8
<223> OTHER INFORMATION: synthetic peptide

<400> SEQUENCE: 8

Ser Ile Ile Asn Phe Glu Lys Leu
1               5
```

TOOL FOR THE TRANSFER AND PRODUCTION OF PROTEINS USING THE PSEUDOMONAS TYPE III SECRETION SYSTEM

CROSS-REFERENCE TO RELATED APPLICATIONS

This application is a Continuation-in-Part of PCT international application serial number PCT/FR2004/050564, filed Nov. 4, 2004 and published in French on Jun. 2, 2005 as publication number WO 2005/049644, which claims priority from French application FR 0313286, filed Nov. 13, 2003. The disclosures of these priority applications and all patents, published applications and other references cited herein are hereby incorporated by reference in their entirety into the present application.

BACKGROUND OF THE INVENTION

The invention relates to a new tool for transfer in eukaryotic cells or a tool for production in the bacterial culture supernatant of chimeric proteins from the type III secretion system present in the *Pseudomonas* bacteria, especially *Pseudomonas aeruginosa*. More precisely, the invention relates to new chimeric protein expression vectors, or more generally amino acid sequences in *P. aeruginosa*. It also relates to *P. aeruginosa* strains transformed with the said expression vectors to secrete or inject using TTSS in *P. aeruginosa*, chimeric proteins in the culture supernatant or in the eukaryotic cells respectively. Thus an in vitro or ex vivo injection method (also called translocation) of chimeric proteins in eukaryotic cells, as well as a chimeric protein production method in the culture supernatant, methods that can be used for therapeutic purposes also form an object of this invention.

Bacteria naturally possess protein secretion systems enabling them to send enzymes or toxins at distance. In addition to these systems, some of them also possess a "type III" secretion system (called TTSS) that allow them to directly inject toxic proteins from their cytosol into the cytosol of a target cell. This secretion mechanism is complex and comprises a certain number of elements that form a canal cutting across the inner membrane, periplasmic space and the outer membrane of the bacteria. This canal allows the transfer of specific toxins. In most species of bacteria, this secretion system can be activated either by contact with a target eukaryotic cell, that triggers the injection of toxins into the cytosol of the target cell, or by $Ca^{2+}$ chelation in the outer medium, that triggers the secretion of specific toxins in the culture medium.

It is thus interesting to study whether these type III secretion systems (TTSS) can be used to inject proteins of interest into eukaryotic cells by fusing the nucleotide sequence encoding the toxin secreted by the TTSS with a second nucleotide sequence encoding a protein of interest.

A TTSS was described in the *Yersinia* bacteria by Cornelis et al. (*Molecular Microbiology* 23(5), 861-867 1997). This document indicates that the type III secretion system of *Yersinia enterocolitica*, called Ysc, is capable of secreting and then translocating effector proteins mainly YopE and YopH in the host cell. Sory et al. (*Proc. Natl. Acad. Sci. USA* 92, 11998-12002 1995) studied the molecular structure of Yop proteins and highlighted the presence of three domains in YopE and YopH, a N-terminal domain for secretion, a domain for translocation and a C-terminal region responsible for the toxic activity of the said protein. These properties were highlighted by constructing hybrid proteins obtained by fusing the amino-terminal part of YopE or YopH with a reporting enzyme, such as adenylcyclase activated by calmodulin, the enzyme activity being measured subsequently.

Moreover, U.S. Pat. No. 5,965,381 indicates the advantage of precisely identifying the minimum size of the nucleotide sequence encoding the effector protein required for secretion and subsequent transfer of a target protein into an eukaryotic cell. The method described to perform this is similar to the previously mentioned method that involves fusing sequences containing a decreasing number of nucleotides with a sequence encoding a reporting enzyme activated by calmodulin, the appearance of cyclase activity in the cytosol of the translocated cell showing the existence of translocation. Even if it is concluded from the description that the constructions were carried out from the first 50, 71, 100 and 130 amino acids of YopE, only the 130 amino acid fragment is illustrated, which means that the other identified amino acid sequences are too small to allow secretion and subsequent translocation of the protein of interest. Consequently, a high number of amino acids required for secretion (130 amino acids) limit, if not prohibit the possible use of this sequence for transferring large-size proteins of interest.

U.S. Pat. No. 6,306,387 describes the presence of a type III secretion system in the *Salmonella* bacteria. This document especially illustrates the possibility of translocating into host cells, a chimeric protein named SptP-NPc obtained by fusing the 173 amino acid N-terminals constituting the toxic protein SptP, naturally secreted by the type III system of *Salmonella* with a partial sequence encoding an Influenza virus nucleoprotein, with the detection being carried out using antibodies capable of detecting the chimeric protein in the infected cell. Even in this case, the amino acid sequence of the injected toxic protein is relatively long as it comprises as much as at least 173 amino acids, thus prohibiting the transfer of large fused proteins into the host cell. Since the injected proteins were not cleaved at a later stage, it is essential to use a toxic protein having the smallest possible size.

The existence of a type III secretion system was also illustrated in a third genus of bacteria, *Pseudomonas*, especially of type *Pseudomonas aeruginosa*. *P. aeruginosa* is a Gram-negative bacillus, and an opportunistic pathogen responsible for serious nosocomial infections in hospitals. It is also one of the main causes of morbidity and mortality in people suffering from mucoviscidosis. The type III secretion system of *P. aeruginosa* is a very effective defence especially against phagocytes, mainly neutrophil granulocytes, the first line defence in cellular immunity. This system is also used by the bacteria to trigger the proliferation and apoptosis of T lymphocytes. It is known that *P. aeruginosa* secretes four toxins, namely ExoS, ExoT, ExoY and ExoU using the type III secretion system.

ExoS is a protein comprising approximately 454 amino acids; sequences for ExoS are known and published in the NCBI GenBank, for example, accession nos. NP252530, AAK39624, AAK38480, AAK38452, AAK38479, AAK38436, AAK34869, AAK38419, AAK38477, AAK38421, AAK37418, AAK38437, AAK38420, AAK38478, AAK38417, CAA67834, AAG07228, and AAA66491. Ahead of the gene encoding ExoS, there is a nucleotide sequence that may encode a molecular chaperone protein supposedly specific to ExoS, named "Orf 1". ExoS possess an ADP-ribosylation activity on small Ras family G-proteins, as well as the capacity to activate the Rho-GTPases. ExoT possess an ADP-ribosylation activity as well but is 100 times inferior to ExoS. Moreover, it is known that 75% of the nucleotide sequences of ExoT and ExoS are identical (according to the LFASTA programme, W. R. Pearson & D. J.

Lipman PNAS (1998) 85:2444-2448). The mode of action of ExoU is unknown but involves a powerful cytotoxin on the epithelium and macrophages.

Polack et al. (*Biochemical and Biophysical Research Communications* 275, 854-858, 2000) refers to a natural isolated strain of *P. aeruginosa*, whose characteristics are not mentioned (CHA strain). The strain is transformed with a pBP31 plastid mainly containing two fused nucleotide sequences, corresponding respectively to the nucleotide sequence encoding the 129 amino acid N-terminals of ExoS and the sequence encoding the $p67^{phox}$ protein involved in reconstituting the NADPH oxidase enzyme complex. Polack showed the capacity of this transformed strain to not only secrete the p67 protein but also to reconstitute the NADPH oxidase activity, following injection of the fused protein into the cytosol of EBV-B lymphocytes, thus illustrating the intracellular activity of the injected proteins. The 129 AA sequence of ExoS used by Polack is thus the smallest sequence ever described for injecting target proteins.

SUMMARY OF THE INVENTION

Applicant has discovered that the secretion and injection of protein into a host cell is possible by using the even smaller ExoS sequences of *P. aeruginosa*, respectively the 48 (SEQ ID 4) to 96 (SEQ ID 6), optimally the first 54 (SEQ ID 5) amino acid N-terminals of ExoS, and any sequence that is at least 70% identical thereto, optimally 75% such as the corresponding amino acid sequence of ExoT. Moreover, the Applicant showed that the secretion and injection was more efficient when smaller sequences were used. From these results, it can be concluded that the nucleotide sequence of ExoS can be optimally modified to encode at least the 48 AA N-terminals of ExoS, and a maximum of the first 96 AA N-terminals of ExoS such that the transformed *P. aeruginosa* strains with the said modified nucleotide sequence may be used either for injecting large proteins into the cytosol of the host cell, or for secreting proteins in the culture medium for their production.

Consequently, the invention relates firstly to a vector for expressing a chimeric protein whose N-terminal end corresponds to the fusion between the N-terminal end of ExoS of *P. aeruginosa* and an amino acid sequence of interest, the N-terminal end of ExoS corresponding to the N-terminal end of the chimeric protein. The said vector is characterized in that it contains the following from 5' to 3':
   a promoter,
   a nucleic acid comprising a nucleotide sequence encoding at least the 48 and at the most the 96 amino acids of the N-terminal end of ExoS, optimally the 54 amino acids, or any sequence of the same size, that is at least 70% identical thereto and that has a secretion activity at the same level as that of ExoS,
   a nucleic acid comprising a nucleotide sequence encoding the amino acid sequence of interest.

In one embodiment, the nucleic acid encodes the first 54 amino acids of the N-terminal end of ExoS (SEQ ID 5).

In one embodiment, the amino acid sequence of interest is an antigenic sequence.

In a related aspect, the invention relates to a cloning vector comprising from 5' to 3':
   a promoter,
   a nucleic acid comprising a nucleotide sequence encoding at least the 48 (SEQ ID 4) and at the most the 96 (SEQ ID 6) amino acids of the N-terminal end of ExoS, or any sequence of the same size, that is at least 70% identical thereto and that has a secretion activity at the same level as that of ExoS.

In one embodiment, the cloning vector comprises a nucleic acid that encodes the first 54 (SEQ ID 5) amino acids of the N-terminal end of ExoS.

In yet another aspect, the invention relates to a chimeric protein whose N-terminal end comprises at least the 48 (SEQ ID 4) and at the most the 96 (SEQ ID 6) amino acids of the N-terminal end of ExoS of *P. aeruginosa* or any sequence of the same size, that is at least 70% identical thereto and that has a secretion activity at the same level as that of ExoS. In one embodiment, the chimeric protein the N-terminal end of the chimeric protein comprises the first 54 (SEQ ID 5) amino acids of the N-terminal end of ExoS of *P. aeruginosa*.

In another related aspect, the invention relates to an isolated strain of *Pseudomonas aeruginosa* transformed with the expression vector of the invention. The strain can be modified by deletion or mutation of at least one gene selected from the genes encoding the ExoS, ExoT, ExoU and ExoY proteins. One embodiment of the strain has been deposited at CNCM (Institut Pasteur de Paris) under the number I-3090.

In yet another aspect, the invention relates to a gene encoding the chimeric protein of the invention.

The invention further relates to a procedure for ex vivo or in vitro injection of a chimeric protein into a eukaryotic cell comprising bringing into contact the isolated strain of the invention with a eukaryotic cell. A procedure for in vivo injection of a chimeric protein into a eukaryotic cell comprising the injection of the strain into a living organism is also encompassed by the invention. In one embodiment, the eukaryotic cell is an antigen presenting cell (APC). Thus, the present invention also provides for an APC-loading procedure, wherein the chimeric protein is introduced into antigen presenting cells.

Accordingly, the present invention provides for a method for stimulating the immune system of a mammal as well as a method for vaccinating a mammal, comprising introducing antigens into APC of said mammal according to the procedure described herein.

In yet another aspect, the invention relates to a procedure for producing a chimeric protein comprising the steps of:
   cultivating a strain according to the invention;
   inducing secretion of the chimeric protein; and
   recovering the culture supernatant.

DETAILED DESCRIPTION OF THE INVENTION

Figure 1:
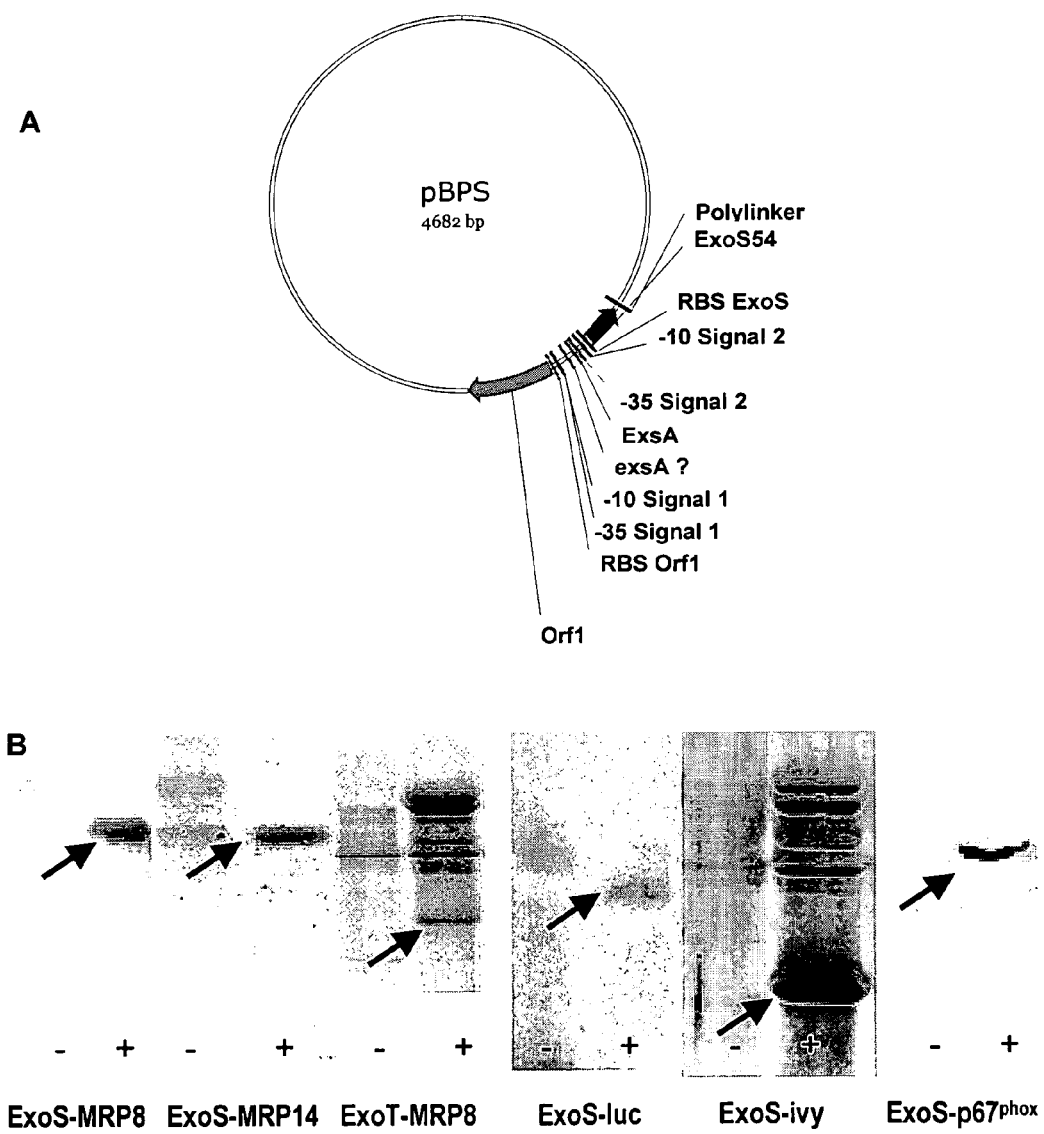
FIG. 1: A) The pBPS54 plasmid created by inserting in the pUCP20 plasmid [2] sequences encoding the first 54 amino acid N-terminals of ExoS and the Orf1 molecular chaperone, while preserving the polylinker to facilitate cloning. B) Secretion of fusion proteins with (+) and without (−) induction of TTSS.

In practicing the present invention, many conventional techniques in molecular biology and recombinant DNA technology are used. Such techniques are well known and are explained fully in, for example, Sambrook et al., 2000, Molecular Cloning: A Laboratory Manual, Third Edition, Cold Spring Harbor Laboratory Press, Cold Spring Harbor, N.Y.; Current Protocols in Molecular Biology, Volumes I, II, and III, 1997 (F. M. Ausubel, ed.)

In the description that follows and in the claims, the expression "amino acid sequence of interest" refers to any amino acid sequence of at least 8 amino acids forming a peptide, a polypeptide, or a natural or synthetic protein, showing a biological activity of industrial pharmaceutical (therapeutic or diagnostic) or agri-food industry interest. For instance, such sequences may correspond to sequences encoding tumour antigens, pathogenic agent antigens, anti-tumour, anti-inflammatory, antiangiogenic and anti-oxidant proteins, antibodies, epitopes, cytokines, cytokine receptor, transcription factor, intercellular communication factors, enzymes or enzyme complex elements.

In a preferred embodiment, the amino sequence of interest is an antigenic sequence.

Similarly the expression "sequence that is at least 70% identical thereto" refers to a sequence containing at least 70%, optimally 75% of AA identical to the 48, 96 or 54 AA of ExoS. In fact, it has been observed that 75% of the nucleotide sequence of ExoT is identical to the nucleotide sequence ExoS, this percentage being obtained from the above-cited LFASTA programme. Moreover, this structural similarity was confirmed by the secretion activity of ExoT, which, as will be seen later, is at the same level as that of ExoS.

In other words, the nucleotide sequence of the expression vector contains two fused nucleotide sequences, a first sequence encoding a sequence comprising the first 48 to 96, optimally the first 54 amino acid N terminals of ExoS, and a second sequence encoding the amino acid sequence of interest.

The two sequences are fused using techniques known to those skilled in the art and, more precisely described in Sambrook.

According to another characteristic, the promoter may be a TTSS promoter or any other inducible promoter or otherwise.

However, the vector may include other elements such as a 3' terminal sequence (including a stop codon) or an antibiotic-resistance gene.

The expression vector is created using techniques perfectly mastered by those skilled in the art, especially by ligating the nucleotide sequence encoding the AA sequence of interest in a cloning vector encoding the N-terminal end of ExoS, more specifically the 48 to 96 AA, optimally the 54 AA of the N-terminal end of ExoS.

Consequently, a cloning vector that contains the following from 5' to 3' also forms an object of the invention:
 a promoter,
 a nucleotide sequence encoding at least the 48 and at the most the 96 amino acids, optimally the first 54 amino acids of the N-terminal end of ExoS, or any sequence of the same size, that is at least 70% identical thereto and that has a secretion activity at the same level as that of ExoS.

The cloning vector may contain other elements, such as a nucleotide sequence encoding a cleavage site allowing the elimination of the N-terminal end of ExoS in the chimeric protein, or at least one cloning site allowing any protein of interest to be cloned.

Chimeric proteins whose N-terminal end is made of the first 48 to 96 aa, optimally the first 54 aa of the N-terminal end of ExoS, or any sequence of the same size, that is at least 70% identical thereto and that has a secretion activity at the same level as that of ExoS, also constitutes a part of the invention.

The gene encoding the aforementioned chimeric protein also forms an object of the invention.

The invention also relates to an isolated strain of *P. aeruginosa*, transformed with the expression vector described hereinabove. This strain can be used either for producing the chimeric protein in the culture supernatant, or for transferring the chimeric protein into the target cell, subsequent to contact with the aforesaid target cell.

It is understood that all transformation techniques known to those skilled in the art can be used such as electroporation, triparental conjugation, bacteriophage transfection, etc.

Moreover, the Applicant aimed at improving the secretion and transfer of the chimeric protein by reducing the toxicity of strains by modifying at least one gene encoding the ExoS, ExoT, ExoU or ExoY proteins such that ExoS and/or ExoT are rendered incompetent for their production or secretion by the TTSS system. In practice, modifications involve mutations or deletions.

In a specific embodiment, the strain on which the transformation is carried out corresponds to the CHA-003 strain filed at the CNCM (INSTITUT PASTEUR, 25 rue du Docteur Roux, F-75724 Paris cedex 15) under the number I-3090 on 17 Sep. 2003, derived from the CHA strain [3], and in which the genes encoding exotoxin S (exoS) and exotoxin T (exoT) were inactivated. This strain possesses the following advantages as compared to the parent CHA strain: toxicity reduced by 20% as compared to CHA and a 10 fold improved secretion and/or injection performance.

Thus, the invention also relates to an isolated strain of *Pseudomonas*, optimally *P. aeruginosa*, whose at least one gene encoding the ExoS, ExoT, ExoU or ExoY proteins is modified by deletion or mutation. In a specific embodiment, the mutated *Pseudomonas* strain corresponds to the aforementioned CHA-003.

As already mentioned the natural function of TTSS know till this day lies in injecting proteins into the cytosol of eukaryotic cells.

Thus, the invention also relates to an in vivo, ex vivo or in vitro injection procedure into an eukaryotic cell of a chimeric protein according to the invention or encoded by a vector according to the invention involving bringing the strain according to the invention in contact with the eukaryotic cell.

Concerning the in vivo injection procedure, the strain according to the invention is injected into the intact living organism.

In the description that follows and in the claims, the expression "eukaryotic cells" refers to human or animal eukaryotic cells used in vitro, ex vivo or in vivo for research, diagnostic or therapeutic purposes.

In a specific embodiment, the eukaryotic cell is an antigen presenting cell (APC).

Therefore, the invention also concerns an APC-loading procedure comprising bringing into contact antigen presenting cells with a vector according to the invention encoding an antigenic sequence.

Another TTSS application, which is not described in the prior art, consists in using the said system for producing chimeric proteins in the culture supernatant by the bacteria.

Consequently, a chimeric protein production procedure whose N-terminal end corresponds to the fusion between the ExoS N-terminal end of *Pseudomonas aeruginosa* and an amino acid sequence of interest, the N-terminal end of ExoS corresponding to the N-terminal end of the chimeric protein also forms an object of the invention, the said procedure consisting in:
 cultivate a strain according to the invention
 induce the secretion of the chimeric protein, and
 recover the culture supernatant.

As mentioned previously, the use of *Pseudomonas*, optimally *Pseudomonas aeruginosa* is preferred for transformation, whose at least one gene encoding the ExoS, ExoT, ExoU or ExoY proteins, optimally ExoS and ExoT is inactivated.

In a specific embodiment, the strain used is the CHA-003 strain.

The induction of chimeric protein secretion can be obtained by Ca$^{2+}$ depletion or by any other method activating the TTSS: foetal calf serum, human or any other serum, Congo red or any other medium.

In practice, the bacteria are cultured until an optimal production of chimeric protein is attained.

Lastly, the supernatant is recovered by any method know to those skilled in the art such as centrifugation, filtration and derived methods. The protein of interest can be subsequently purified by using any protein purification technique know to those skilled in the art such as affinity chromatography, ion exchange, exclusion, immunoprecipitation, etc.

As demonstrated below, the invention allows efficient antigen delivery to antigen presenting cells (APC) in mammals. Therefore, the present invention also concerns methods for stimulating the mammal immune system, for vaccinating a mammal and/or for treating a mammal comprising the injection of a strain according to the invention in order to introduce antigens into APC of said mammal. These methods are very promising, specially in the field of cancers, for tumor treatment or prevention, e. g. for immunotherapy of glioma.

The invention and its derived advantages can be better appreciated through the following embodiments.

EXAMPLE 1

Secreting properties of ExoS and ExoT

This example shows that a protein of interest can be produced and secreted by P. aeruginosa when it is fused with the first 54 amino acids of ExoS or ExoT. The genes encoding the proteins of interest, e.g. MRP8, MRP14, XylE, IVY, p67phox are cloned in phase with the sequence encoding the toxins secreted by TTSS, e.g. ExoS and ExoT. This sequence, optimally encoding the first 54 amino acids, is placed under the control of the natural promoter of the said toxin. The entire construction is carried by a plasmid that replicates in P. aeruginosa (FIG. 1A).

The plasmid is introduced by electroporation in a P. aeruginosa strain. The bacteria are cultivated either in the absence of TTSS induction (LB medium) or in the presence of 5 mM EGTA, 20 mM MgCl$_2$ that allow the induction of protein synthesis and their secretion in the supernatant. The analysis of culture supernatants in the absence or presence of induction of secretion is carried out in polyacrylamide gel in denaturing conditions (SDS-PAGE) after the precipitation of proteins from 1 ml of supernatant with 10% perchloric acid. Development is carried out by staining with Coomassie blue for MRP8, MRP14 and IVY, and with silver nitrate for Luc and P67phox. In tracks with induction (marked +), the presence of a strip whose migration corresponds well to the size of the expected protein (arrow) is observed. In terms of quantity, the best secretion is obtained for the Ivy protein fused with ExoS-54, enabling the production of about 10 microG of protein for 1 ml of supernatant. For most proteins tested, a production yield ranging from 0.5 to 10 mg of protein for one liter of supernatant is obtained.

EXAMPLE 2

Injection Properties of ExoS

This example demonstrates that a protein of interest can be produced and injected into a cell of interest by P. aeruginosa when it is fused with the first 54 amino acids of ExoS. The genes encoding the protein of interest, e.g. P67phox, MRP8 and MRP14 are cloned in phase with the sequence encoding the toxins secreted by the TTSS, e.g. ExoS and ExoT. This sequence, optimally encoding the first 54 amino acids, is placed under the control of the natural promoter of the said toxin. The entire construction is carried by a plasmid that replicates in P. aeruginosa.

Figure 2A:
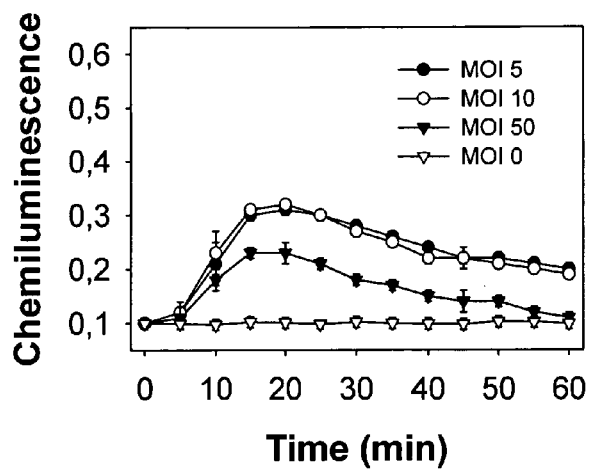
FIG. 2: A) Measuring production of superoxide anion by the GZ B lymphocyte line (deficient in $p67^{phox}$ in presence or absence of plasmid containing the ExoS54-$p67^{phox}$ fusion. B) Measuring production of superoxide anion by the normal lymphocyte line with 1) the plasmid control, 2) a plasmid expressing ExoS54-MRP8, 3) a plasmid expressing ExoS54-MRP14, 4) the two plasmids.
Figure 2B:
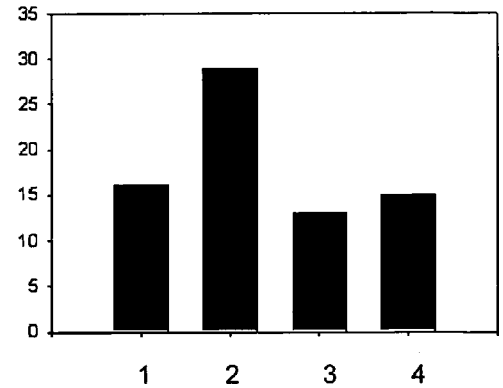

The plasmid is introduced into a P. aeruginosa strain by electroporation. The bacteria are cultivated in a LB medium in absence of TTSS induction and are brought into contact with the target eukaryotic cell (B lymphocytes for p67phox). The bacteria/eukaryotic cell ratio (MOI) is 1:50, optimally 10. After one hour of co-culture, the NADPH oxidase activity resulting from the transduction of the above-described proteins is measured by the production of superoxide ions on the entire cells by chemiluminescence as described in the article [3]. The FIG. 2A shows the effect of the infection ratio on the injection efficiency. The production kinetics of the superoxide ion by the modified B lymphocytes is in favour of the infection ratio ranging between 5 and 10. Most experiments show that the optimal infection ratio is 1:10 for the different types of transformed lines (lymphocytes, neutrophils, macrophages, granulated PLB985 lines, dendritic cell, etc.).

The example 2B shows that this in vitro injection procedure can be used to measure the respective and/or concomitant effects of two or more proteins of interest. The bar 1 shows the basal level activity in relative chemiluminescence unit when normal B lymphocytes are brought in contact with the CHA-003 carrying a control plasmid that does not contain the gene of interest. The bar 2 shows the increase in NADPH oxidase activity when the ExoS54-MRP8 protein is injected by the bacteria (MOI=10) that contains a construction encoding an ExoS54-MRP8 fusion protein. The bar 3 shows the absence of increase in the NADPH oxidase basal activity during injection of the ExoS54-MRP14 fusion protein by the bacteria. The bar 4 shows the inhibition of increase in the NADPH oxidase activity, when the cells are incubated in presence of the two previously described strains and allow the expression of ExoS54-MRP8 and ExoS54-MRP14.

This system also allows the concomitant injection of one, two or several proteins.

EXAMPLE 3

Improvement of Secretion with ExoS54

The optimal sequence length of ExoS allowing secretion was determined by using constructions of variable length fused with the XylE protein whose catechol dioxygenase enzyme activity was measured in the culture supernatant [4].

Figure 3:
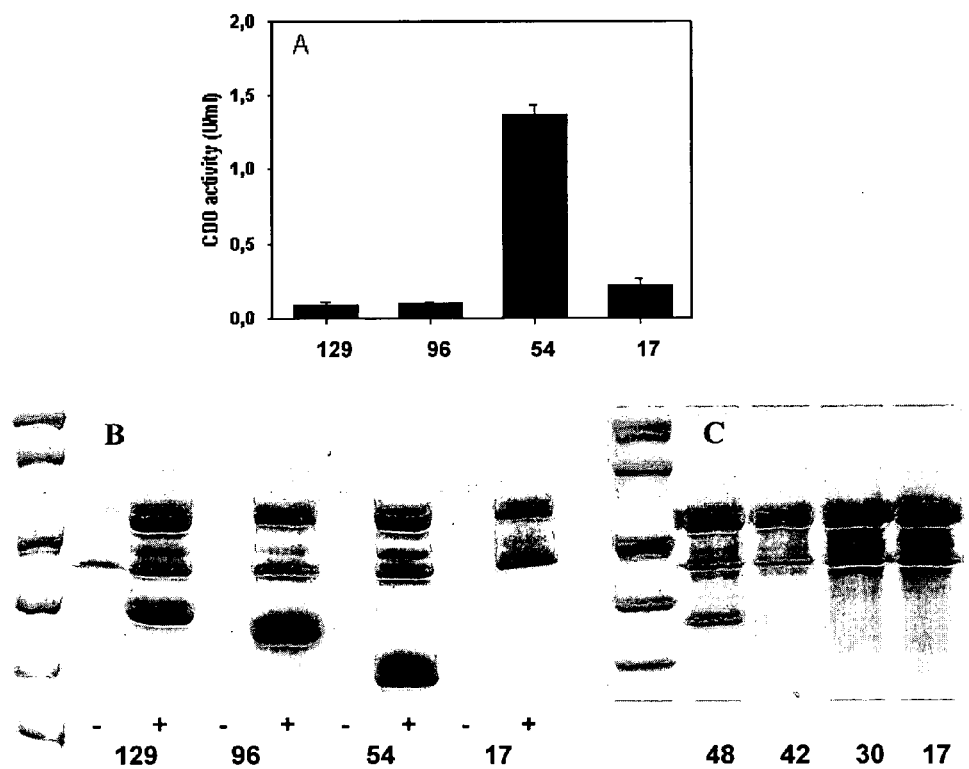
FIG. 3: A) CDO activity measured in supernatants obtained after bacterial culture by inducing secretion by the ExoS-XylE fusions with the first 129 (SEQ ID7), 96, 54 and 17 amino acids of ExoS. B) and C) The ExoS-MRP8 fusion proteins secreted in the supernatant are separated by polyacrylamide gel electrophoresis in the presence of SDS et stained with Coomassie blue. The panel A represents ExoS-MRP8 fusions with the first 129, 96, 54 and 17 amino acids of ExoS with induction of secretion (+) and without induction of secretion (−) of TTSS. The panel C represents ExoS-MRP8 fusions with the first 48 (SEQ ID4), 42 (SEQ ID3), 30 (SEQ ID2) and 17 (SEQ ID1) amino acids of ExoS with induction of secretion of TTSS.

The CHA-003 strain was transformed with different plasmids allowing the expressions of ExoS-XylE fusions containing the first 129 (SEQ ID 7), 96, 54 and 17 (SEQ ID1) amino acids of ExoS. The reduction from 129 to 54 amino acids of ExoS enables at least a 6-fold increase in the CDO activity measured in the culture supernatant. Same results were obtained with the MRP8 protein. The FIG. 3B was obtained with the MRP8 protein instead of XylE. The transformed bacteria are activated to secrete the fusion proteins by calcium depletion for 3 hours. 1 ml of culture supernatant is precipitated using perchloric acid for 1 hour as described hereinabove. The proteins are separated in polyacrylamide gel in presence of SDS and stained with Coomassie blue. For MRP8, the fusions 129, 96 and 54 allow an excellent secretion. However, FIG. 3C shows that the ExoS-MRP8 secretion stops when less than 48 amino acids of ExoS are used. The examples of XylE (3A) and MRP8 (3B and C), as well as other tested proteins show that a fusion with the first 54 amino acids of ExoS proves optimal for most proteins.

EXAMPLE 4

Improvement of Injection with ExoS54

Figure 4:
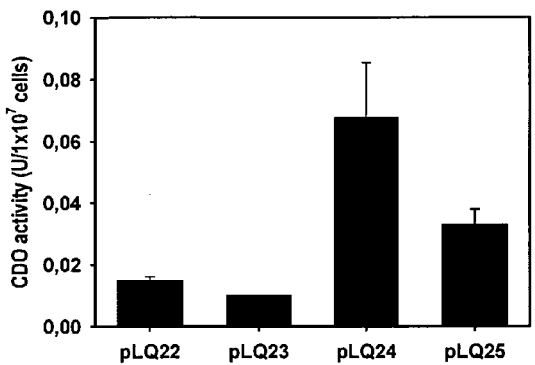
FIG. 4: CDO activity measured in the cytosol of PLB985 cells following one hour of bacteria/cell co-culture in a 10:1 ratio. The bacteria contain plasmids encoding the XylE fusions with the first 129 (pLQ22) 96 (pLQ23) 54 (pLQ24) and 17 (pLQ25) amino acids of ExoS.

The optimal sequence length of ExoS allowing injection into eukaryotic cells was also determined by using constructions of variable length fused with the XylE protein whose catechol dioxygenase enzyme activity was measured in the cytosol of PLB985 cells after one hour of bacteria/cell co-culture in a ratio of 10:1. As expected, since secretion is optimal with the first 54 amino acids of ExoS, the injection follows the same rules (FIG. 4). The ExoS54 sequence can thus be used as the universal label enabling secretion or injection of proteins of interest for research, diagnostic or therapeutic purposes.

EXAMPLE 5

Improvement of Strain

Figure 5:
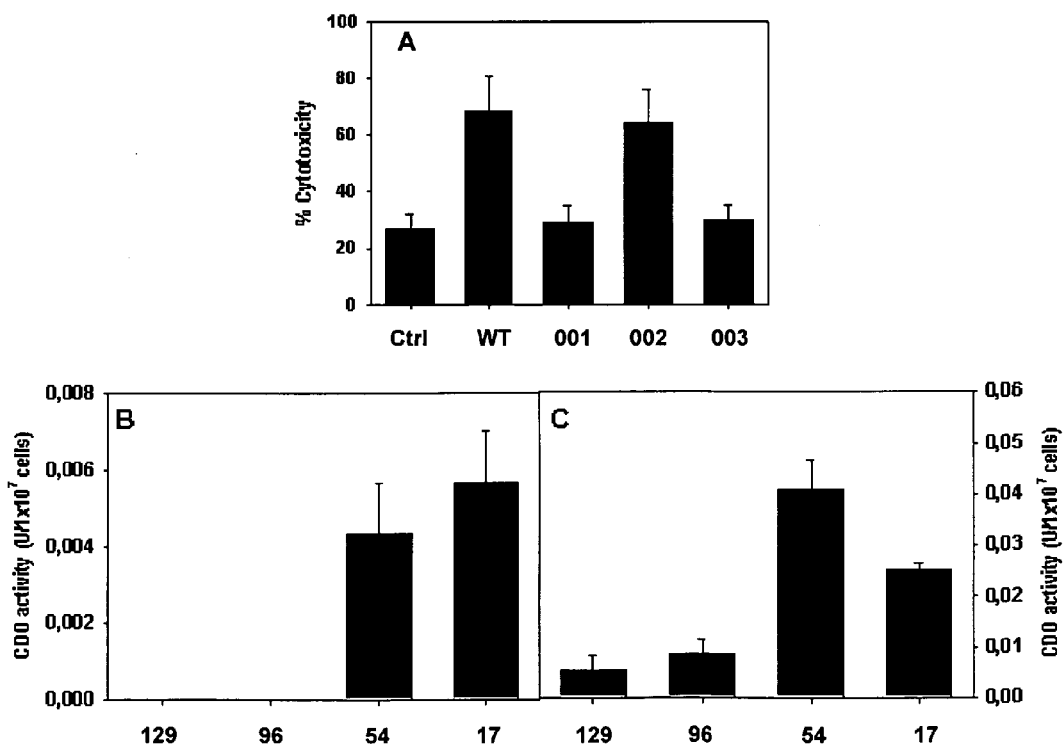
FIG. 5: A) Toxicity of wild strain (WT) and mutants deleted in the TTSS toxins CHA-001 deleted for exoS, CHA-002 deleted for exoT and CHA-003 deleted for exoS and exoT. B) and C) Quantification using XylE of the injection of the CHA wild strain (B) and CHA-003 deleted in ExoS and ExoT (C). This injects 10 times more than the wild strain.

The improvement of strain was initially carried out to avoid the cytotoxicity phenomena during the use of TTSS to inject proteins into mammalian cells. This is why the first criterion retained was the reduction of natural toxicity in the CHA strain owing to the ExoS and ExoT toxins. Different inactivation mutants were obtained by the invalidation of genes according to methods known to those skilled in the art [5]. These methods involve inserting either a deletion or an interruption of the reading frame within the gene to be inactivated. The modified gene takes the place of the wild gene during a simple or double recombination experiment by any method known to those skilled in the art. The strains thus obtained no longer allow the expression of targeted genes. From the CHA strain (wild), CHA-001 deleted in exoS, CHA-002 deleted in exoT and CHA-003 deleted in exoS and ExoT were obtained. Their toxicity to target cells was measured (FIG. 5). The toxicity of these strains on several cells (PLB985 granulocyte line, human neutrophils, murine macrophages, and dendritic cells) was measured during bacteria-cell co-culture experiments at different infection ratios during incubation periods ranging from one to four hours, by measuring the lactate dehydrogenase secreted by the cell plaques under the toxic action of the bacteria. All results are compiled in FIG. 5A that shows a clear decrease in the toxicity that becomes comparable to the noise when exoS and exoT are inactivated.

Since the ExoS and ExoT toxins are also transported by the TTSS, the effect of this inactivation was measured to improve the injection of the protein of interest. The ExoS54-XylE construction was introduced into the different mutants and the bacteria were co-cultured with the PLB985 cell at a ratio of 10, enabling the injection gain to be quantified. A 10-fold improvement in the injection was obtained due to the use of the CHA-003 strain deleted in ExoS and ExoT.

EXAMPLE 6

Injection Procedure

From a research, diagnostic or therapeutic perspective, it can be advantageous to directly inject the proteins of interest into a population of mammalian cells using the TTSS of *P. aeruginosa*. The injection procedure described herein below can be applied to cells in culture or to whole live organisms when the toxicity arising from the injection of *P. aeruginosa* can be tolerated. This procedure can be applied to all types of protein. The various steps of the procedure may have to be optimised depending on the protein and/or cell type to be transformed. The main optimisations may concern: infection ratio to be used, co-culture time, medium used for co-culture. The procedure can be outlined as follows for cells in culture.

The gene encoding the protein of interest is cloned in phase with the N-terminal part of ExoS or ExoT, optimally with the first 54 amino acids of ExoS. All types of plasmids replicating in *P. aeruginosa*, and allowing the expression of such fusions are used. For instance, the one described in example 1.

The plasmid is introduced into a *P. aeruginosa* strain, optimally the CHA-003 strain, by electroporation or any other method known to those skilled in the art. The bacteria are cultured in a LB medium in the absence of TTSS induction until the middle of the exponential phase of growth. The bacteria are then recovered by centrifugation, washed and re-suspended in the culture medium used for the mammalian cells to be transformed. The bacteria are brought into contact with the target cells. The bacteria/eukaryotic cell ratio (MOI) is 1:50, optimally 10. After an hour of co-culture, the bacteria can be eliminated by washing and addition of antibiotics into the culture medium. The produced phenotype can then be observed or the cells put back into culture should the produced phenotype require a longer period of action.

Example: Intracytosolic Injection of a Human Protein into Human B Lymphocytes

Using the TTSS of *P. aeruginosa*, an active protein capable of reconstituting a highly regulated enzyme complex assembly, the NADPH oxidase, was injected into the cytosol of cells from patients carrying this enzyme deficiency. The NADPH oxidase produces superoxide radicals that destroy the pathogenic microorganisms during the phagocytic metabolic explosion. This enzyme is also present in other cells including B lymphocytes immortalised by the Epstein-Barr virus (EBV B lymphocytes). The activation of NADPH oxidase involves the assembly of 4 cytosolic proteins ($p47^{phox}$, $p67^{phox}$, $p40^{phox}$ and a small monomeric G protein Rac1 or Rac2) with a heterodimeric transmembrane glycoprotein, the flavocytochrome $b_{558}$ composed of two sub-units, $p22^{phox}$ and $gp91^{phox}$. Molecular anomalies in the genes encoding $p47^{phox}$, $p67^{phox}$, $p22^{phox}$ or $gp91^{phox}$ cause a severe disease called chronic granulomatous disease (CGD) characterised by the absence of superoxide anion production on the biochemical level, and by severe and repetitive bacterial infections putting the vital prognosis of the patient at stake despite antibiotics on the clinical level. A patient whose phagocytes and EBV B-lymphocytes are incapable of producing superoxide ions was used as the model. These cells neither express the $p67^{phox}$ m-RNA nor this protein. Since the $p67^{phox}$ is a cytosolic factor, this model was used to analyse and validate the vectorial transport of proteins into the cytosol and the capacity of transferred proteins to be activated and inserted into a multi-molecular enzyme complex whose activation regulation involves the interactions of highly sophisticated molecules.

Figure 6:
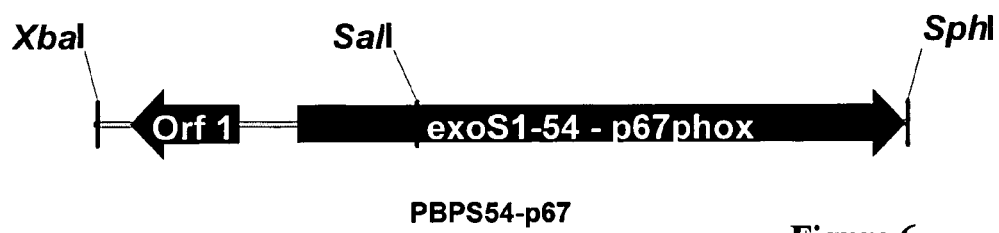
FIG. 6: The pBPS54-p67 plasmid encodes a hybrid protein comprising the N-terminal domain of the ExoS protein fused with the NADPH oxidase cytosolic factor, p67$^{phox}$. The SalI-SphI cloning cassette allows in-phase insertion of the protein of interest.

The vectors were developed from the bacteria *P. aeruginosa* (CHA-003 strain). The pBPS54-p67 plasmid was created, encoding the ExoS-p67$^{phox}$ hybrid protein, comprising the first 54 amino acid N-terminals of ExoS fused with the amino acid N-terminal of p67$^{phox}$. This construction is placed before the natural promoter of ExoS, and the entire structure is carried by the pUCp20 plasmid. The molecular chaperone specific to ExoS, Orf1, is included in its initial orientation to optimise the cytosolic transfer of the chimeric protein (FIG. 6).

Figure 7:
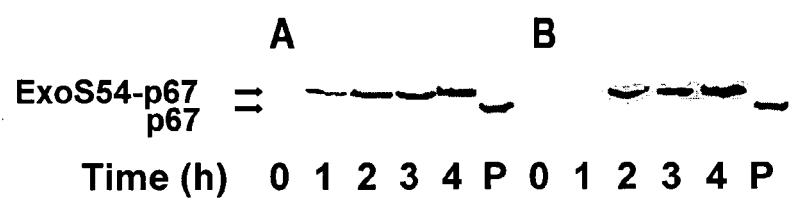
FIG. 7: Biosynthesis and secretion of ExoS-p67$^{phox}$ by CHA-p31 after stimulation by calcium chelation. The ExoS-p67$^{phox}$ protein hybrid is detected by Western blot with an antibody directed against the C-terminal end of p67$^{phox}$ either in the packed bacterial cells lysed with ultrasound (A) or in the culture medium (B). P corresponds to the native p67$^{phox}$ protein, purified from phagocytes.

The CHA-003 strain of *P. aeruginosa* containing the pBPS54-p67 plasmid synthesises and secretes the hybrid protein after stimulation by calcium chelation (FIGS. 7A and B). The hybrid protein is thus synthesised and secreted in the same condition as the native ExoS protein.

By Western blot using the anti $p67^{phox}$ antibody, it was verified that the hybrid protein ExoS-$p67^{phox}$ is also injected into the cytosol of EBV B Lymphocytes. The cytosolic concentration attained is comparable to that of the endogenous protein $p67^{phox}$. This cytosolic injection is well dependant on the type III secretion system.

Figure 8:
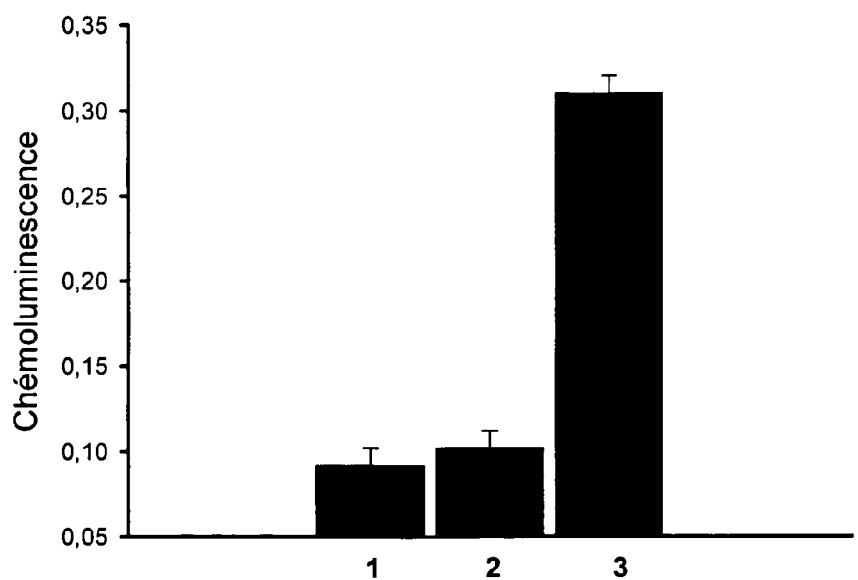
FIG. 8: Functional reconstitution of NADPH oxidase in the GZ EBV B lymphocyte line deficient in p67$^{phox}$. Production of superoxide anion at the 15th minute of incubation by lymphocytes deficient in p67$^{phox}$. 1) only lymphocytes deficient in p67$^{phox}$, 2) lymphocytes deficient in p67$^{phox}$ in the presence of the CHA strain, 3) lymphocytes deficient in p67$^{phox}$ in presence of the CHA-003 strain containing the pBPS54-p67 plasmid with an infection ratio of 10.
Figure 9:
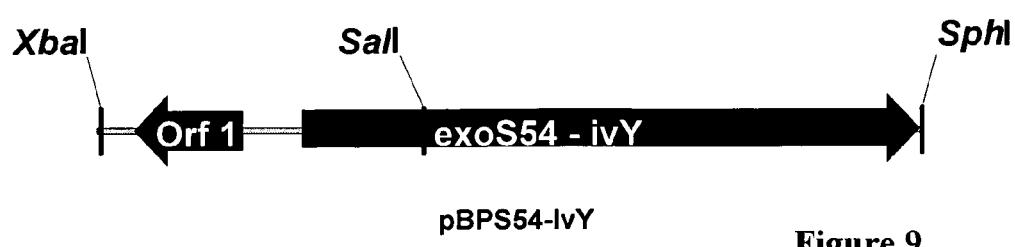
FIG. 9: The pBPS54-ivY plasmid encodes a hybrid protein comprising the N-terminal domain of the ExoS protein fused with the inhibition factor of the IVY lysozyme of *P. aeruginosa*. The SalI-SphI cloning cassette allows in-phase insertion of the protein of interest.

An in vitro reconstitution experiment of the NADPH oxidase activity indicates that the hybrid protein keeps all its functional domains accessible. Several other factors are involved within the cells. In fact, the cellular protein traffic is physiologically triggered during their synthesis in the endoplasmic reticulum and continues during the maturation of the protein through the different parts of the Golgi apparatus to finally end at their site of action, which may be the nucleus, one of the intracellular organelles or one of the cytosolic compartments. A partially understood complex area code allows in fine the mature protein to be localised in the subcellular compartment, where it plays its role. The self-addressing capacities of a hybrid molecule such as ExoS-$p67^{phox}$ in the sub-membrane compartment, where the final assembly of the NADPH oxidase probably lies were tested ex vivo on normal EBV B-Lymphocytes and EBV B-Lymphocytes deficient in $p67^{phox}$, the GZ cellular line. When the GZ line is incubated with 5, 10 or 50 bacteria per cell (MOI), 40 to 50% of the enzyme complex activity is restored (FIG. 8).

EXAMPLE 7

Production Procedure

Most recombinant proteins can be obtained from bacteria such as *Escherichia coli*, or from eukaryotic cells (yeast, insect or mammalian cells). However, experiments have shown that a number of proteins cannot be obtained from these standard production hosts either because their expression is toxic for the production host, or because of degradation owing to the bad folding of the protein due to unfavourable conditions in the production host. The use of type III secretion system of *P. aeruginosa* allows the expression and direct secretion of proteins into the culture supernatant. This system is thus well adapted to the production of recombinant proteins having either an intracellular toxicity, or a production or folding defect inside the bacteria. It has been demonstrated in the various examples of this patent that the production yield can reach 10 mg per liter of culture. However, when the CHA-003 strain that does not secrete the S and T exotoxins is used, the protein produced becomes the main product in the culture supernatant, thus simplifying the later purification stages.

The example given is that of the Ivy protein encoding a lysozyme inhibition factor in bacteria. This protein in obtained with great difficulty in its recombinant form in *E. coli*. The gene encoding the Ivy protein of *P. aeruginosa* was amplified by PCR using primers containing cloning sites in phase with the first 54 amino acids of ExoS.

The pBPS54-Ivy plasmid was introduced by electroporation in the CHA-OO3 strain. The bacteria were cultured overnight at 37° C., and then diluted in the morning in fresh LB medium in presence or absence of EGTA that allows calcium depletion and thus the induction of TTSS.

Figure 10:
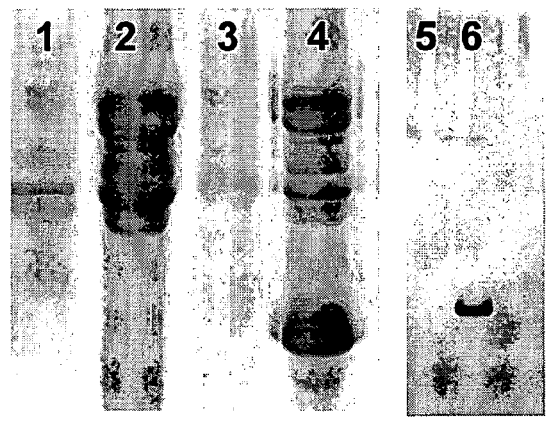
FIG. 10: Production of the ExoS-IVY protein. 1 ml of supernatant before or after induction had been precipitated by perchloracetic acid and analysis in SDS-PAGE gel and stained with Coomassie blue. 1/non-induced CHA strain, 2/induced CHA strain, 3/non-induced CHA strain containing the pBPS54-ivY plasmid, 4/induced CHA strain containing the pBPS54-ivY plasmid. The same protein with a polyhistidine label is purified in an immobilised nickel affinity column: 5/washing after fixation on IMAC column by 10 mM imidazol, 6/elution with 300 mM imidazol.

The strip shown with an arrow in FIG. 10 track 4 migrates to a size of 22 kDa and corresponds to a quantity in the order of 10 µg of protein per ml of supernatant, i.e. 10 mg/l. When the protein bears a poly-histidine label, its purification by immobilised nickel affinity chromatography (IMAC) can be carried out directly from the culture supernatant after induction and dialysis to eliminate EGTA. FIG. 10 track 6 shows the presence of a single strip corresponding to the hybrid protein purified in the IMAC column eluate.

EXAMPLE 8

A Live Attenuated TTSS-Based Vector for Anti-Tumor Prophylactic and Curative Immunotherapy I—Introduction:

It had been projected that in 2004, ≈18,400 new cases of primary brain cancer would be diagnosed in the United States and 12,690 people would die of the disease. In terms of biology, treatment, and prognosis, brain tumors are a heterogeneous group of neoplasms. Malignant gliomas are the most common of these brain tumors and have a high mortality rate and short median length of survival (40.9 weeks).

Actually, the most successful treatment for cancer is still surgery. However, this therapy is active only for some small-sized not disseminated tumors, and when a total surgical exeresis is achievable. For most patients, adjuvant chemotherapy is recommended. However, despite the use of new and expensive single and combination drugs to improve response rates and other agents to allow for dose escalation, there has been no change in some of the regimens used, and there has been little impact from the use of newer regimens. In 1986, the estimated contribution of chemotherapy to overall survival in the USA was 4.3%. In 2004, Morgan et al. estimated it to be between 2.1 and 2.3%.

Immunotherapeutic approaches are becoming important for the treatment and prevention of various human diseases such as cancer. The generation of tumor-specific T cytotoxic lymphocytes (CTL) is the main goal of anti-tumor immunotherapy strategies. Several factors including efficient antigen delivery to antigen presenting cells (APC) above a threshold level and antigen presentation are crucial for efficient anti-tumor immunity. Both of these conditions can be achieved using either gene therapy or protein therapy, but with many limitations.

By 2003 over 790 human gene therapy trials had been approved since the first one in 1989. The major targets of these efforts were cancer (66% of the total) and monogenic disorders (10% of the total). In 70% of the cases, viral vectors, mainly of retroviral or adenoviral origin, were used for gene delivery, but viral vectors have several drawbacks. The random integration of the vector DNA into the genome may lead to carcinogenesis, and the spread of the viral vector into nontarget organs may result in a toxic immunological reaction. Non-viral gene delivery also poses challenges regarding tissue targeting, transfection efficiency, instability of the DNA after delivery into the cytosol, transport of the DNA into the nucleus, and stable integration of the DNA into the genome.

In contrast to gene therapy, the goal of protein therapy is to deliver therapeutic peptides or proteins instead of DNA into target cells. Although this approach is currently limited by the selectivity and poor permeability of the cell membrane, there is a growing effort to design new strategies for protein delivery into cells. Protein transduction domains (PTDs) have been shown to allow proteins to efficiently cross biological membranes independently of transporters or specific receptors and to allow antigen delivery to APCs. The limitations of this method include the requirement to fuse the target protein to a PTD and the need in some cases to denature the target protein prior to delivery. Furthermore, fusion to a PTD may interfere with the function of the therapeutic peptide or protein.

Several Gram-negative bacteria have a complex protein secretion apparatus designated the type three secretion system (TTSS) to deliver effector proteins into the cytoplasm of eukaryotic cells in order to modulate host cellular functions. Here we propose to take advantage of the TTSS of *Pseudomonas aeruginosa* to deliver tumor antigens to APCs to generate a specific CTL response against antigen-expressing tumors. Already more than 100 years ago bacteria were used in the treatment of cancer. Indeed some bacteria such as *Bifidobacterium, Clostridium*, and *Salmonella* have been shown to preferentially replicate within solid tumors, and Bacille Calmette-Guerin (BCG) and Listeria have been evaluated as cancer immunotherapies. The potential of live, attenuated bacteria as vaccines and vectors has long been recognized and offers several advantages including their own immunogenicity.

The bacterial vector according to the invention presents two main advantages. First, specific antigen can be delivered to dendritic cells (DC) by the TTSS. Second, APCs are exquisitely sensitive to bacterial determinants such as lipopolysaccharide and flagellin. Therefore, a strong immune response against the antigen-expressing tumor cells is obtained.

STATEMENT OF DEPOSIT

A deposit of an isolated *Pseudomonas aeruginosa* strain containing the bacterial vector of the invention was made prior to the filing date of the above-identified patent application under the terms of the Budapest Treaty. The deposit was made with the Collection Nationale de Cultures de Microorganismes (CNCM) INSTITUT PASTEUR, 25, Rue du Docteur Roux, F-75724, Paris Cedex 15 on Sep. 17, 2003 and has been assigned the Patent Deposit Designation Number CNCM 1-3090.

II—Procedures and Results:
Engineering of the Bacterial Vector

Figure 11:
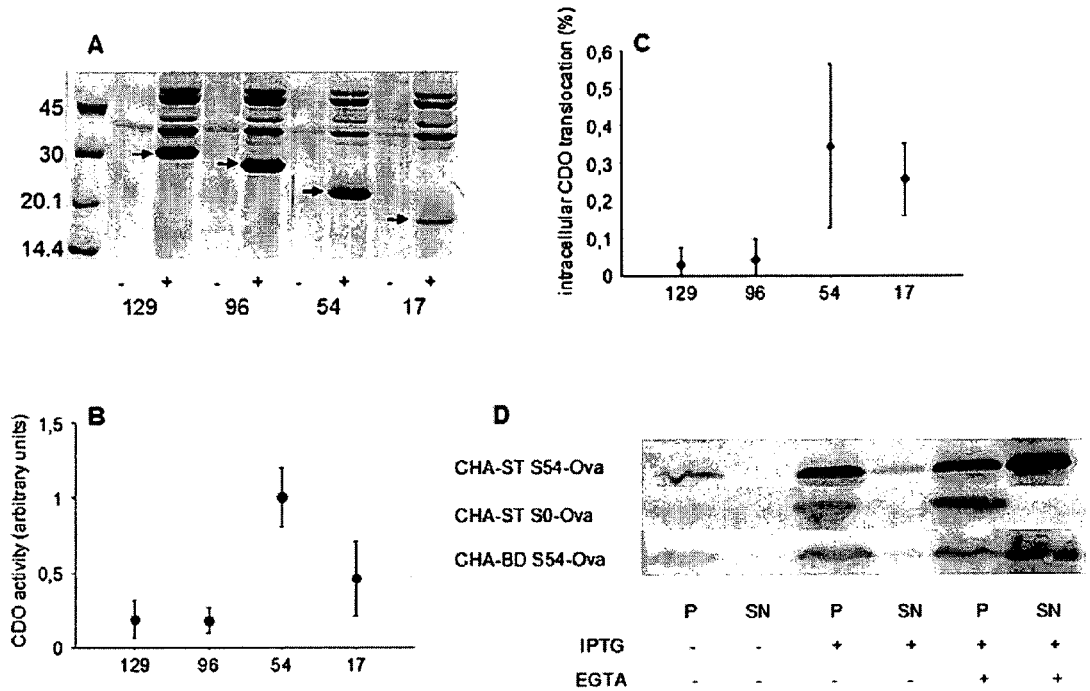
FIG. 11: Type III secretion system analysis. A—Secretion of ExoS-IVY. SDS-PAGE of culture supernatants of CHA strains transformed with pS(129, 96, 54 or 17)-IVY (*P. aeruginosa* inhibitor of vertebrate lysozyme) and grown in the absence (−) or presence (+) of TTSS activation. Theoretical molecular weights of the fusion proteins are 30.7 kDa for ExoS129-IVY, 27.1 kDa for ExoS96-IVY, 23.1 kDa for ExoS54-IVY, and 18.8 kDa for ExoS 17-IVY. The arrows indicate the positions of the fusion proteins. B—Secretion of ExoS-CDO. CHA strains transformed with pS(129, 96, 54 or 17)-CDO (*P. putida* catechol 2-3 dioxygenase) were grown in the presence of TTSS activation. The CDO activity in the culture supernatant was measured with a spectrophotometric assay. Each point represents the average of three independent experiments. Error bars represent a 95% CI. C—Translocation of ExoS-CDO. CHA strains transformed with pS(129, 96, 54 or 17)-CDO were incubated with myeloid cells for 1 h. CDO activity in cells and in the bacteria was measured with a spectrophotometric assay. The results are expressed as the ratio (cell activity/bacteria activity)×100. Each point represents the average of three independent experiments. Error bars represent a 95% CI. D—Western blot of pellets (P) and supernatants (SN) from cultures of CHA-OST S54-Ova, CHA-OST S0-Ova, and CHA-BD S54-Ova grown either without supplementation, with IPTG, or with both IPTG and TTSS activation (EGTA). ExoS-Ova fusion proteins were detected with an anti-ovalbumin polyclonal antibody.

For the secretion of the *Yersinia* TTSS toxins, the N-terminal 15 to 17 amino acids (aa), are sufficient, however, a similar domain is not described for other bacterial pathogens. Therefore the region of *P. aeruginosa* TTSS toxin Exoenzyme S (ExoS) required for the secretion and translocation was determined by generating protein fusions between the N-terminal 129, 96, 54, or 17 aa of ExoS and reporter proteins that are not normally secreted by the TTSS. High secretion levels were observed when each of the reporter proteins was fused with the N-terminal 54 aa of ExoS (FIGS. 11A and 11B; see also example 3). In addition, when fused to the N-terminal 54 aa of ExoS, cytoplasmic delivery of CDO was also optimal (FIG. 11C).

The TTSS toxins ExoS and Exoenzyme T (ExoT) are involved in *P. aeruginosa* pathogenesis. To reduce CHA cytotoxicity, an attenuated CHA-OST mutant (ExoS$^-$, ExoT$^-$) was developed. This corresponds to strain CHA-003 in example 5. The viability of bone marrow-derived myeloid DCs from C57BL/6 mice was assessed 24 h after a 1 h exposure to either CHA or CHA-OST. With the parental strain 50% of the DCs were killed whereas the survival rate was 95% in the presence of CHA-OST.

To control fusion protein expression in *P. aeruginosa*, the exsA gene encoding the ExoS transcriptional activator was cloned under the control of an isopropyl-β-D-thiogalactopyranoside (IPTG) inducible promoter. Addition of IPTG to the culture resulted in an increase of the intrabacterial level of S54-Ova (a fusion between the N-terminal 54 aa of ExoS and the C-terminus of ovalbumin), and high-level secretion of S54-Ova (FIG. 11D).

As negative control for antigen delivery, we elaborated secretion or translocation negative strains. Mutant CHA-BD lacking TTSS structure proteins PopB and PopD allows protein secretion (FIG. 11D) but not translocation. S0-Ova (lacking ExoS N-terminal sequence) was produced but was not secreted (FIG. 11D).

Subsequently, antigen delivery to DCs was evaluated in vitro and in vivo with four strains: (i) CHA-OST S54-Ova (secreting and translocating the antigen by TTSS), (ii) CHA-OST S0-Ova (not secreting nor translocating the antigen), (iii) CHA-BD S54-Ova (secreting but not translocating the antigen, and (iv) CHA-OST S54-GFP (secreting and translocating GFP as control antigen).

In vitro Evaluation of the Vector

Figure 12:
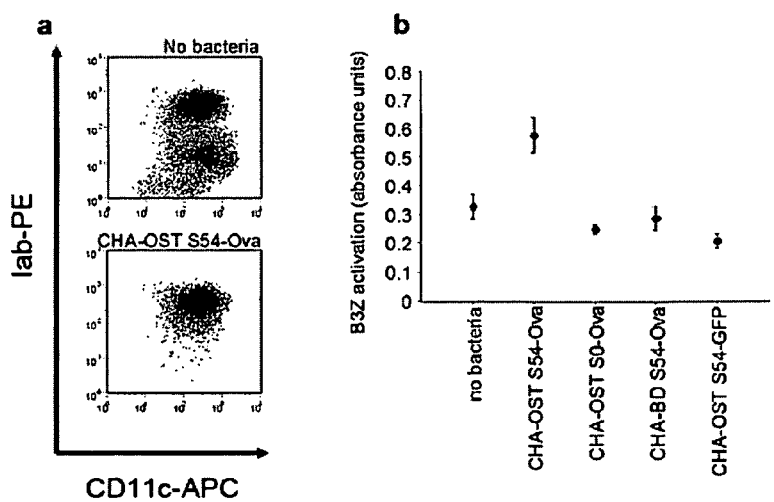
FIG. 12: In vitro DC activation and peptide presentation to specific lymphocytes. A—FACS analysis of C57BL/6 DCs activation at 24 h after a 1 h incubation with or without CHA-OST. The dot plots are representative of repeated experiments. B—B3Z hybridoma activation by C57BL/6 DCs previously incubated with different bacterial strains as indicated. The B3Z T cell receptor is specific to the ovalbumin peptide SIINFEKL (SEQ ID NO.: 8) presented by mice MHC-IH-2K.sup.b. B3Z activation was assessed with a .beta.-galactosidase enzymatic assay (absorbance at 570 nm). The vaccine vector (CHA-OST S54-Ova) delivering by TTSS the ovalbumin fragment was compared with 3 control vectors: CHA-OST S0-Ova (not secreting nor translocating ovalbumin), CHA-BD-S54-Ova (secreting but not translocating ovalbumin), CHA-OST S54-GFP (secreting and translocating GFP as control antigen). The data was obtained from three independent experiments in triplicate. The error bars represent a 95% CI.

DCs from C57BL/6 (MHC-I H-2K$^b$) mice incubated for 1 h with CHA-OST strain containing S54-Ova induced by IPTG. It induced within 24 h a maturation and activation of more than 90% of DCs (FIG. 12A).

To evaluate if exposition to the vaccine vector induces the antigen presentation by DCs to specific CD8+T lymphocytes, DCs from mice incubated for 3 h with the four bacterial strains were incubated with B3Z hybridoma cells. B3Z cells have a T cell receptor (TCR) specific to the ovalbumin 257-264 peptide (SIINFEKL) (SEQ ID NO.: 8) presented by MHC-I H-2K.sup.b. TCR-mediated B3Z activation was obtained after incubation with DCs that had been exposed to CHA-OST S54-Ova (FIG. 12B). No activation was observed after exposure of DCs to phosphate buffer saline (PBS), CHA-OST S0-Ova, CHA-BD S54-Ova, or CHA-OST S54-GFP (FIG. 12B). The results demonstrated that specific antigen delivery via the *P. aeruginosa* TTSS was well suited for MHC-I presentation.

In vivo Evaluation of the Vector

Figure 13:
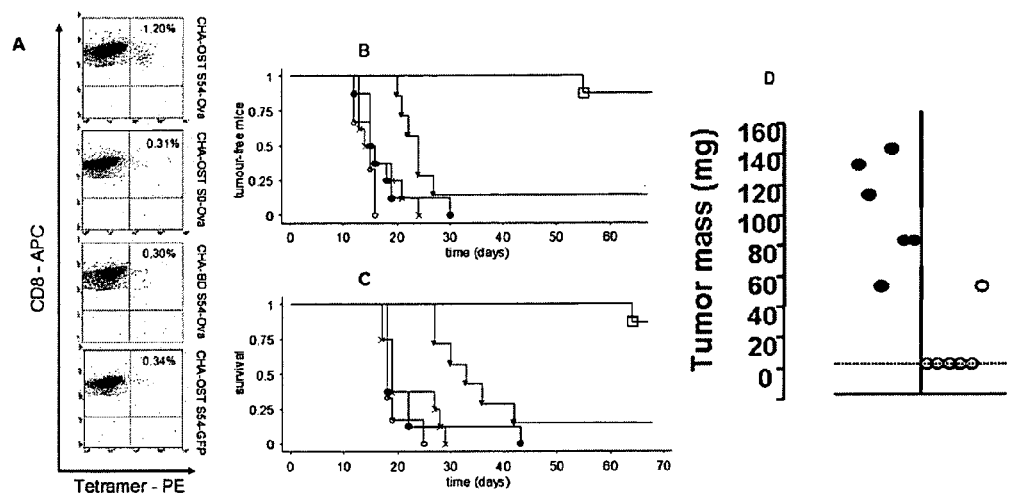
FIG. 13: In vivo activity of *P. aeruginosa* vector. The vaccine vector (CHA-OST S54-Ova) was compared with the same controls than in FIG. 2B. A—Quantification of specific anti-ovalbumin peptide SIINFEKL (SEQ ID NO.: 8) CD8+T lymphocytes among freshly harvested splenocytes in C57BL/6 mice injected with different bacterial strains at 13 and 5 d before analysis. The cells were quantitated by flow cytometry using anti-CD8-FITC and H-2K.sup.b-ovalbumin.sub.257-264 (SIINFEKL) tetramer-PE. Dead cells were excluded from analysis after viability assessment using propidium iodide staining. The dot plots are representative of repeated experiments in different animals. B, C-In vivo tumor challenge with B16-Ova (at day 0) in C57BL/6 mice injected 14 and 7 days before with different bacterial vectors: .quadrature., CHA-OST S54-Ova, n=8; O, CHA-OST S0-Ova, n=6; , CHA-BD S54-Ova, n=7; .times., CHA-OST S54-GFP, n=8; , PBS, n=8. B-Delay of visible tumor onset. C—Mouse survival. D, B16-Ova were intravenously injected at day 0. Mice were vaccinated at day 5 and 12 and the mass of lung metastasis analyzed at day 17.

To assess the ability of the bacterial vector to raise in vivo, C57BL/6 mice were injected with 5×10$^6$ bacteria at day 1 and 8, and splenocytes were harvested at day 13 and screened for specific CD8+T lymphocytes by staining with anti-CD8+ and H-2K$^b$-ovalbumin$_{257-264}$ (SIINFEKL; SEQ ID NO:8) tetramer. Up to 1.2% of the CD8+T lymphocytes were specific for SIINFEKL (SEQ ID NO:8) in mice injected with CHA-OST S54-Ova as compared to 0.3% of the CD8+T lymphocytes in mice injected with one of the other strains (FIG. 13A).

The first model used to evaluate a vaccine effect of our bacterial vector was the mouse melanoma cell line B16-OVA that expresses chicken egg ovalbumin. Injection of B16-OVA cells into syngenic C57BL/6 mice results in rapid tumor development.

In a prophylactic approach, C57BL/6 mice were subcutaneously injected with either 5×10$^6$ bacteria or PBS at both 14 and 7 d before subcutaneous injection of 2×10$^5$ B16-OVA cells. Only 1 of 8 mice injected with CHA-OST S54-Ova developed a tumor; It was 55 days after injection of B16-OVA tumor cells (FIGS. 13B and 13C). All mice injected with PBS, CHA-OST S0-Ova, or CHA-OST S54-GFP developed a tumor within 3 weeks after injection of B16-OVA tumor cells (FIGS. 13B and 13C). Mice injected with CHA-BD S54-Ova had a delayed kinetic of tumor formation (FIGS. 13B and 13C).

In addition, a curative model of pulmonary metastasis was also evaluated. 5×10$^5$ B16-OVA cells were injected to C57BL/6 mice by the intravenous route of the retro-orbitary plexus. Then, mice were subcutaneously injected with either 5×10⁶ bacteria or PBS both 5 and 12 d after tumor injection. At 17 d, mice were euthanized and lungs were removed for macroscopic evaluation of metastasis. Metastasis were dissected and weighted (FIG. 13D).

Figure 14:
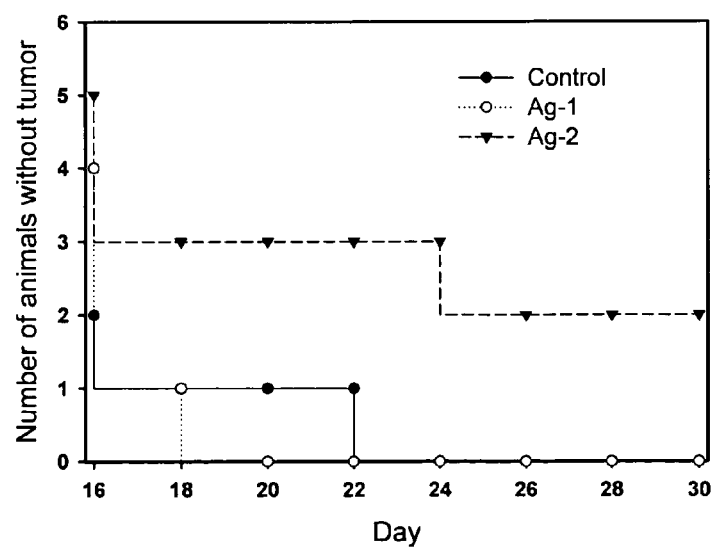
FIG. 14: Vaccination in the GL26 mice glioma subcutaneous model. Animal, 6 per group, were vaccinated using two different antigens and followed for up to 30 days. Tumor growth in mice vaccinated with Ag-2 was reduced by 50% (p<0.0001, ANOVA).

These results obtained with the melanoma B16 cell line were extended to glioma GL26 cell line, aiming at glioma therapy. Vaccination against intrinsic antigens in a mice subcutaneous glioma model (FIG. 14) showed that only one of the two selected proteins endogenously expressed by the tumor cells had a significant effect on tumor development. Since both proteins were similarly secreted by the vaccine bacterial strain, it is necessary to evaluate the immune response induced by specific antigen.

III—Conclusions:

Vectors for anti-tumor immunotherapy need to deliver antigen to the MHC-I presentation pathway and to exhibit TLR ligands. The TTSS-based *Salmonella* vector, by providing both requirements, resulted in protective immunity in a viral infection model. However, we demonstrated for the first time the effectiveness of a live attenuated TTSS-based vector for anti-tumor prophylactic and curative immunotherapy. Antigen delivery by the TTSS was demonstrated in vitro and in vivo by the protection induced by CHA-OST S54-Ova compared with a strain deficient in protein secretion and translocation (CHA-OST S0-Ova) or one deficient in protein translocation (CHA-BD S54-Ova). For these strains, antigen may have been delivered to APCs by phagocytosis or pinocytosis but not processed for MHC-I restricted presentation.

The strengths of the claimed vector are its simple administration route and its flexibility to translocate a variety of proteins. The subcutaneous injection of a live antigen-delivering bacteria may allow the immune system to develop a more complete immune response toward the antigen than the reaction obtained with ex vivo manipulated DCs. The S54-Ova fusion protein has a molecular weight of 19.9 kDa, but larger proteins were also correctly secreted and translocated. This property will allow immunization protocols with entire antigenic proteins, which provide panel of putative epitopes at once. This offers the possibility of a wide usage in vaccination, bypassing the limitation associated to the use of short peptides as antigens which are restricted to peculiar MHC-I alleles. Clinical phase I trials using live attenuated bacteria have been conducted and these vectors may be acceptable for human therapy. Therefore they may become an important tool for the activation of specific CD8+T lymphocytes in association with existing therapies for cancer patients.

REFERENCES

1. CORNELIS et Al. (1997) Mol. Microbiol. 23(5).
2. SORY et Al. (1995), Proc. Natl. Acad. Sci. USA 92:11998-12002.
3. POLACK, B., VERGNAUD, S., PACLET, M. H., LAMOTTE, D., TOUSSAINT, B., MOREL, F.: Protein delivery by *Pseudomonas* type III secretion system: Ex vivo complementation of p67$^{phox}$ deficient chronic granulomatous disease. Biochem. Biophys. Res. Commun. 275, 854-858, 2000.
4. SAMBROOK J., Russel D W, Molecular cloning, a laboratory manual, 3$^{rd}$ edition, Cold Spring Harbor Laboratory Pres, CSH 2001.
5. DELIC-ATTREE, I., TOUSSAINT, B., VIGNAIS, P. M.: Cloning and sequence analyses of the genes coding for the integration host factor (IHF) and HU proteins of *Pseudomonas aeruginosa*. Gene 154, 61-64, 1995.
6. WEST, S. E. H., SCHWEIZER, H. P., DALL, C., SAMPLE, A. K., RUNYEN-JANECKY, L. J.: Construction of improved *Escherichia-Pseudomonas* shuttle vectors derived from pUC18/19 and sequence of the region required for their replication in *Pseudomonas aeruginosa*. Gene 128, 81-86, 1994.
7. KONYECSNI, W. M., DERETIC, V.: Broad-host-range plasmid and M13 bacteriophage-derived vectors for promoter analysis in *Escherichia coli* and *Pseudomonas aeruginosa*. Gene 74, 375-386, 1988.
8. SCHWEIZER, H. P., HOANG, T. T.: An improved system for gene replacement and xylE fusion analysis in *Pseudomonas aeruginosa*. Gene 158, 15-22, 1995.

The invention claimed is:

1. A vector for expression of a chimeric protein that is a fusion between the N-terminal end of either ExoS or ExoT of *Pseudomonas aeruginosa* and a protein of interest, said vector comprising the following from 5' to 3':
    a promoter; and
    a nucleic acid that encodes the chimeric protein, the chimeric protein consisting of the first 54 amino acids of the N-terminal of ExoS (SEQ ID NO.: 5) or the first 54 amino acids of the N-terminal of ExoT and said protein of interest.

2. The vector of claim 1, wherein the the protein of interest comprises an antigenic sequence.

3. An isolated strain of *Pseudomonas aeruginosa* transformed with the expression vector of claim 1.

4. The strain of claim 3, wherein said *Pseudomonas aeruginosa* strain is modified by deletion or mutation of at least one gene selected from the genes encoding the ExoS, ExoT, ExoU and ExoY proteins.

5. The strain of claim 3, wherein the strain has been deposited at CNCM (Institute Pasteur de Paris) under the number I-3090.

6. An APC (antigen presenting cell)-loading procedure comprising bringing into contact the strain according to claim 3 with the APC.

7. A procedure for producing the chimeric protein comprising the steps of:
    cultivating the *Pseudomonas aeruginosa* strain of claim 3 comprising the chimeric protein under conditions wherein the chimeric protein is expressed; and
    recovering the chimeric protein from a culture supernatant.

8. A cloning vector comprising from 5' to 3':
    a promoter, and
    a nucleic acid that encodes a chimeric protein consisting of the first 54 amino acids of the N-terminal end of ExoS (SEQ ID NO.: 5), or the first 54 amino acids of the N-terminal of ExoT, and a protein of interest.

9. An isolated nucleic acid that encodes a chimeric protein consisting of the first 54 amino acids of the N-terminal end of ExoS (SEQ ID NO.: 5) of *Pseudomonas aeruginosa* or the first 54 amino acids of the N-terminal of ExoT of *Pseudomonas aeruginosa*, and a protein of interest.

* * * * *